US012680994B2

(12) United States Patent     (10) Patent No.:   US 12,680,994 B2

Lu     (45) Date of Patent:     Jul. 14, 2026

(54) CARBON AND OXYGEN ISOTOPE RATIOS TO IDENTIFY SOURCE ROCKS

(71) Applicant: Saudi Arabian Oil Company, Dhahran (SA)

(72) Inventor: Feng Hu Lu, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 387 days.

(21) Appl. No.: 18/464,842

(22) Filed: Sep. 11, 2023

(65) Prior Publication Data

US 2024/0159723 A1     May 16, 2024

Related U.S. Application Data

(60) Provisional application No. 63/425,105, filed on Nov. 14, 2022.

(51) Int. Cl.
    *G01N 1/44*       (2006.01)
    *G01N 33/00*     (2006.01)

(52) U.S. Cl.
    CPC ........... *G01N 33/0055* (2013.01); *G01N 1/44* (2013.01)

(58) Field of Classification Search
    CPC ........... G01N 33/0055; G01N 33/0036; G01N 33/0009; G01N 33/0004; G01N 33/00; G01N 1/44; G01N 1/28; G01N 1/00; G01V 9/007; G01V 9/00
    See application file for complete search history.

(56) References Cited

U.S. PATENT DOCUMENTS

| | | | |
|---|---|---|---|
| 2,874,565 | A | 2/1959 | Kelton |
| 5,241,859 | A | 9/1993 | Smith |
| 5,359,194 | A | 10/1994 | Moss |
| 5,388,456 | A | 2/1995 | Kettel et al. |
| 6,898,912 | B2 | 5/2005 | Bravinski |
| 7,704,746 | B1 | 4/2010 | White et al. |
| 8,972,233 | B2 | 3/2015 | Bohacs et al. |
| 9,910,938 | B2 | 3/2018 | Morales German et al. |
| 10,330,659 | B2 | 6/2019 | Dreyfus et al. |
| 10,393,904 | B2 | 8/2019 | Shahri et al. |
| 10,533,414 | B2 | 1/2020 | Lawson et al. |
| 10,823,716 | B2 | 11/2020 | Lu |
| 11,066,929 | B2 | 7/2021 | Lu |

(Continued)

FOREIGN PATENT DOCUMENTS

| | | |
|---|---|---|
| CN | 113252421 B | 9/2021 |
| CN | 110672821 | 3/2022 |

(Continued)

OTHER PUBLICATIONS

Alqahtani, Sedimentology, Sequence Stratigraphy, and Diagenesis of the Lower Wuchiapingian Khuff Unit in a Field in Saudi Arabia, 2019, Thesis, pp. 1-146. (Year: 2019).*

(Continued)

*Primary Examiner* — Mohamed Charioui
(74) *Attorney, Agent, or Firm* — Fish & Richardson P.C.

(57) ABSTRACT

The disclosure relates to methods for identifying desirable (e.g., the best) depth intervals in a formation using carbon and/or oxygen isotope ratio information. The desirable depth intervals in the formation correspond to regions in the formation with source rocks and relatively high (e.g., the highest) total organic carbon (TOC).

20 Claims, 3 Drawing Sheets

(56) References Cited

U.S. PATENT DOCUMENTS

| | | | |
|---|---|---|---|
| 11,105,943 | B2 | 8/2021 | Chen et al. |
| 11,313,224 | B2 | 4/2022 | Hakami et al. |
| 2012/0118565 | A1 | 5/2012 | Trautman et al. |
| 2012/0118879 | A1 | 5/2012 | Rey-Bethbeder et al. |
| 2013/0037707 | A1* | 2/2013 | Lamberti ............. G01N 33/241 |
| | | | 250/288 |
| 2017/0074094 | A1* | 3/2017 | Rowe ................... E21B 49/005 |
| 2019/0048717 | A1* | 2/2019 | Lu .......................... G01N 33/24 |
| 2019/0055842 | A1* | 2/2019 | Lu ........................ G01V 11/005 |
| 2019/0212314 | A1 | 7/2019 | Lu |
| 2023/0138017 | A1 | 5/2023 | Lu |
| 2023/0145385 | A1 | 5/2023 | Lu |
| 2024/0159728 | A1 | 5/2024 | Lu |

FOREIGN PATENT DOCUMENTS

| | | |
|---|---|---|
| EP | 2824455 A1 | 1/2015 |
| EP | 2936134 B1 | 2/2021 |
| ES | 2686601 | 10/2018 |
| WO | WO 2012062592 | 5/2012 |

OTHER PUBLICATIONS

Houst et al. "Depth profiles of carbonates formed during natural carbonation", Jun. 10, 2002, Elsevier Science Ltd., pp. 1923-1930 (Year: 2002).*

Marolf, "Redox-Sensitive Trace Elements Document Chemical Depositional Environment and Postdepositional Oxidation of the Ediacaran Biri Formation, Southern Norway", 2014, Thesis, pp. 1-102. (Year: 2014).*

Vahrenkamp et al., "Carbon-isotope signatures of Albian to Cenomanian (Cretaceous) shelf carbonates of the Natih Formation, Sultanate of Oman," GeoArabia, 2013, 18(3):65-82, 18 pages.

SAIP Examination Report in Saudi Arabian Appln. No. 123450802, mailed on Oct. 12, 2025, 19 pages (with English translation).

SAIP Examination Report in Saudi Arabian Appln. No. 123450801, mailed on Aug. 20, 2025, 22 pages (with English translation).

agilent.com [online], "Autosampler Vials for HPLC & GC," Headspace Vials & Headspace Caps, available on or before Jan. 23, 2022, via Internet Archive: Wayback Machine URL<https://web.archive.org/web/20240000000000*/https://www.agilent.com/en/product/vials-sample-containment/vials-caps-inserts-septa/headspace-vials-caps>, retrieved on Apr. 11, 2024, URL<https://www.agilent.com/en/product/vials-sample-containment/vials-caps-inserts-septa/headspace-vials-caps>, 2 pages.

agilent.com [online], "GC Sample Preparation & Introduction, 7697A Headspace Sampler," available on or before Sep. 20, 2020, via Internet Archive: Wayback Machine URL<https://web.archive.org/web/20240000000000*/https://www.agilent.com/en/product/gas-chromatography/gc-sample-preparation-introduction/7697a-headspace-sampler>, retrieved on Apr. 11, 2024, URL<https://www.agilent.com/en/product/gas-chromatography/gc-sample-preparation-introduction/7697a-headspace-sampler>, 4 pages.

Berner et al., "Maturity related mixing model for methane, ethane and propane, based on carbon isotopes," Org. Geochem. vol. 13, Sep. 25, 1988, 6 pages.

Brand, "Cavity ring-down spectroscopy versus high-temperature conversion isotope ratio mass spectrometry; a case study on $\delta 2H$ and $\delta 18O$ of pure water samples and alcohol/water mixtures," Rapid Commun. Mass Spectrom, May 2009, 1879-1884, 6 pages.

Burruss et al., "Carbon and hydrogen isotopic reversals in deep basin gas: evidence for limits to the stability of hydrocarbons," Org. Geochem., 2010, 41: 1285-1296, 12 pages.

Chi et al., Diagenetic history and porosity evolution of Upper Carboniferous sandstones from the Spring Valley #1 well, Maritimes Basin, Canada-implications for reservoir development, Journal of Geochemical Exploration, vol. 80, No. 2-3, Sep. 1, 2003, 21 pages.

Chiba et al., "Oxygen isotope exchange rate between dissolved sulfate and water at hydrothermal temperatures," Geochimica et Cosmochimica Acta, Apr. 1985, 49(4):1993-1000.

Chung and Sacket, "Use of Stable Carbon Isotope Compositions of Pyrolytically Derived Methane as Maturity Indices for Carbonaceous Materials," Geochimica et Cosmochimica Acta, vol. 43, Dec. 1979, 10 pages.

Dai et al., "Geochemical characteristics of marine and terrestrial shale gas in China," Marine and Petroleum Geology 76 (2016) 444e463, 20 pages.

Dai et al., "Geochemistry of the extremely high thermal maturity Longmaxi shale gas," Sichuan Basin. Org. Geoch., 2014, 74: 3-12, 10 pages.

Dai et al., "Stable carbon and hydrogen isotopes of gases from the large tight gas felds in China," Science China, Earth Sciences, Jan. 2014, 57:1 (88-103), 16 pages.

de Wit et al., "Multiple Organic Carbon Isotope Reversals across the Permo-Triassic Boundary of Terrestrial Gondwana Sequences: Clues to Extinction Patterns and Delayed Ecosystem Recovery," The Journal of Geology 110, No. 2, Mar. 2002, 21 pages.

Dolan, M.P. et al. "Calibrating Stable Carbon Isotopes of Reservoir Fluids As a Thermal Maturity Indicator," AAPG Search and Discovery Article #90092 © 2009 AAPG Rocky Mountain Section, Jul. 9-11, 2008, Denver, Colorado; Abstract only (Year: 2008).

Dromart et al., "Ice age at the Middle-Late Jurassic transition?" Earth and Planetary Science Letters, Aug. 2003, 213:205-217, 17 pages.

Faber, "Zur Isotopengeochemie gasförmiger Kbhlenwasserstoffe," Geochemie, Erdöl Erdgas Kohle 103, May 1987, 9 pages.

Galimov, "Isotope organic geochemistry," Organic Geochemistry, 37(10), pp. 1200-1262, Apr. 2006, 63 pages.

Goddard et al., "Novel Gas Isotope Interpretation Tools to Optimize Gas Shale Production Contract: 08122-15," retrieved from URL http://citeseerx.ist.psu.edu/viewdoc/download?doi=10.1.1.397.4161&rep=rep1&type=pdf, retrieved on April 11, 2019, available on or before Jun. 5, 2013, 90 pages.

Golding, S.D. et al. "Stable isotope geochemistry of coal bed and shale gas and related production waters: A review," International Journal of Coal Geology 120 (2013) 24-40 (Year: 2013).

Grozeva et al., "Chemical and isotopic analyses of hydrocarbon-bearing fluid inclusions in olivine-rich rocks," Philosophical Transactions A, Jan. 2020, 378(2165), 29 pages.

Gurgey et al., "Geochemical and isotopic approach to maturity/source/mixing estimations for nature gas and associated condensates in the Thrace Basin, NW, Turkey," Applied Geochemistry, Pergamon, Amsterdam, vol. 20, No. 11, Nov. 2005, 21 pages.

Hajikazemi et al., "Chemostratigraphy of Cenomania-Turonian Carbonates of the Sarvak Formation, Southern Iran," Journal of Petroleum Geology, Apr. 1, 2012, 17 pages.

Hitzman et al., "Routine staining of drill core to determine carbonate mineralogy and distinguished carbonate alteration textures," Mineralium Deposita, Nov. 1, 1999, 5 pages.

Huang et al., "Natural gas genesis and sources in the Zizhou gas field, Ordos Basin, China," Research Institute of Petroleum Exploration & Development, 2015, 13 pages.

Jarvis et al., "Secular variation in Late Cretaceous carbon isotopes: a new 13C carbonate reference curve for the Cenomanian-Campanian (99.6-70.6 Ma)," Kingston University London, Geological Magazine, Sep. 2006, 143(5), 49 pages.

Jenkyns, "Geochemistry of oceanic anoxic events," Geochem. Geophys. Geosyst., Mar. 2010, 11(3):1-30.

Kim et al., "Influence of dissolved ions on determination of oxygen isotope composition of aqueous solutions using the CO2-H2O equilibration method," Rapid Commun. Mass Spectrom, Jun. 2012, 26:2083-2092, 10 pages.

Laughrey et al., "Limits to Hydrocarbon Stability in Deep Basins: Evidence from Stable Isotope Reversals and Noble Gas Geochemistry," EAGE Shale Workshop Conference, Nice, Paris, Apr. 2010, 2 pages.

Lécuyer et al., Oxygen isotope fractionation and equilibration kinetics between CO2 and H2O as a function of salinity of aqueous solution. Chem., Geol., 2009, 264(1-4):122-126, 5 pages.

Lillis, P.G. et al. "Petroleum systems of the San Joaquin Basin Province—geochennical characteristics of gas types: Chapter 10 in

(56)                    References Cited

OTHER PUBLICATIONS

Petroleum systems and geologic assessment of oil and gas in the San Joaquin Basin Province, California." U.S. Geological Survey. doi:10.3133/pp1713.ch10 (Year: 2008).

Lu, "How long is enough: CO2-H2O equilibration for δ18O analysis in saline formation waters?" Rapid Communication of Mass Spectrometer, Rapid Commun. Mass Spectrom., May 2016, 30, 7 pages.

Lu, "Online high-precision δ2H and δ18O analysis in water by pyrolysis," Rapid Commun. Mass Spectrom, Jul. 2009, 23:3144-3150, 12 pages.

Lu, "Using Isotope Technology to Identify Oil and Gas Reservoir Sweet Spots," SPE Reservoir Characterisation and Simulation Conference and Exhibition, Abu Dhabi, UAE, Jan. 24, 2023, 8 pages.

Nederlof et al. "Understanding Fluid Variations in the Arab Formation in Abu Dhabi: New Technlogies for Detailed Reservoir Fluid Characterisation" Society of Petroleum Engineers 5PE-211618-MS (Year: 2022).

Ni et al., "Fundamental studies on kinetic isotope effect (KIE) of hydrogen isotope fractionation in natural gas systems," Geochimica et Cosmochimica Acta, 2011, 75, 2696-2707, 12 pages.

Norville et al., "Carbon and hydrogen isotopic variations of natural gases in the Southeast Columbus basin offshore southeastern Trinidad, West Indies—clues to origin and maturity," Applied Geochemistry, Pergamon, Amsterdam, vol. 22, No. 9, Aug. 24, 2007, 9 pages.

Peters et al., "Carbon and hydrogen stable isotope variations in kerogen during laboratory-simulated thermal maturation," Am. Assoc. Petrol. Geol. Bull., 1981, 65(3), 501-508, 8 pages.

Retallack and Jahren, "Methane Release from Igneous Intrusion of Coal during Late Permian Extinction Events," University of Oregon, Eugene Oregon, the Journal of Geology, vol. 116, Issue 1, Jan. 2008, 21 pages.

Schmid et al., "Carbon isotope stratigraphy using carbonate cements in the Triassic Sherwood Sandstone Group: Corrib Field, west of Ireland," Chemical Geology, Elsevier Science Publisher B.V. Amsterdam, vol. 225, No. 1-2, 2006, 19 pages.

Sofer et al., Activities and concentrations of oxygen-18 in concentrated aqueous salt solutions: analytical and geophysical implications. Earth Planet Sci. Lett., Jul. 1972, 15(3), 232-238, 7 pages.

Stable Isotopes in Oceanographic Studies and Paleotemperatures, Spoleto 1995, Tongiorgi (ed)., p. 9-130, 63 pages.

Takahata et al., "Precise Isotopic Measurements of Nitrogen at the Sub-Nanomole Level," Analytical Sciences, Jun. 1998, (14):485-491, 7 pages.

Tang et al., "A kinetic model for thermally induced hydrogen and carbon isotope fractionation of individual n-alkanes in crude oil," Geochim. Cosmochim. Acta, 2005, 69(18), 4505-4520, 16 pages.

Tavakoli et al., "Diagenetic controlled reservoir quality of South Pars gas field, and integrated approach," Comptes Rendus—Geoscience, Elsevier, Paris, France, vol. 343, No. 1, Oct. 5, 2010, 17 pages.

thermofisher.com [online], "TriPlus™M 500 GC Headspace Autosampler, Catalog No. 25118200," available on or before Jan. 2, 2020, via Internet Archive: Wayback Machine URL<https://web.archive.org/web/20240000000000*/https://www.thermofisher.com/order/catalog/product/25118200>, retrieved on Apr. 11, 2024, URL<https://www.thermofisher.com/order/catalog/product/25118200>, 3 pages.

Tilley et al., "Gas isotope reversals in fractured gas reservoirs of the western Canadian Foothills: Mature shale gases in disguise," AAPG Bulletin, 2011, 95, 1399-1422, 24 pages.

Wang et al., "Geochemical characteristics and origin of nature gas in southern Jingbian fas field, Ordos Basin, China," Journal of Natural Gas Science and Engineering, Elsevier, Amsterdam, NL, vol. 46, Sep. 9, 2017, 11 pages.

Wang et al., "Raman Geothermometry of Carbonaceous Material in the Basal Ediacaran Doushantuo Cap Dolostone: The Thermal History of Extremely Negative 613C Signatures in the Aftermath of the Terminal Cryogenian Snowball Earth Glaciation,".

Whiticar, "Correlation of natural gases with their sources," AAPG Memoir, vol. 60, Jan. 1994, 23 pages.

Xinyu et al., "Isotopic reversals with respect to maturity trends due to mixing of primary and secondary products in source rocks," Chemical Geology, Elsevier Science Publisher, vol. 339, Aug. 4, 2012, 8 pages.

Zhang et al., "Chemical and isotopic composition of gases released by crush methods from organic rich mudrocks," Organic Geochemistry, May 2014, (73):16-28, 13 pages.

Zou, Caineng, "The Characteristics and Significance of Conventional and Unconventional Sinian-Lilurian Gas Systems in the Sichuan Basin, central China", Mar. 2015; 17 pages.

Zumberge et al., "Isotopic reversal ('rollover') in shale gases produced from the Mississippian and Fayetteville formations," Marine and petroleum geology, 2012, 31: 43-52, 10 pages.

* cited by examiner

CARBON AND OXYGEN ISOTOPE RATIOS TO IDENTIFY SOURCE ROCKS

CROSS-REFERENCE TO RELATED APPLICATIONS

This application claims the benefit of U.S. Provisional Application No. 63/425,105, filed Nov. 14, 2022, the entire contents of which are incorporated by reference in its entirety.

FIELD

The disclosure relates to methods for identifying desirable (e.g., the best) depth intervals in a formation using carbon and/or oxygen isotope ratio information. The desirable depth intervals in the formation correspond to regions in the formation with source rocks and relatively high (e.g., the highest) total organic carbon (TOC).

BACKGROUND

Organic-carbon enriched rocks were deposited during different periods of time in geological history and are source rocks for natural gas, petroleum and/or coal. Source rocks can be found using geophysical tools or seismic attributes to detect high TOC, or by directly measuring TOC from formations.

SUMMARY

The disclosure relates to methods for identifying desirable (e.g., the best) depth intervals in a formation using carbon and/or oxygen isotope ratio information. The desirable depth intervals in the formation correspond to regions in the formation with source rocks and relatively high (e.g., the highest) TOC.

The methods can allow for the discovery of source rocks with relatively large amounts of TOG. The methods can allow for the identification of the location of source rocks relatively quickly and/or inexpensively compared to certain other methods of identifying source rocks.

The methods can allow for the observation of interval(s) with source rocks and high (e.g., the highest) TOC in a formation, which can be relatively hard to identify using certain geophysical methods. Additionally, the interval(s) can be determined and correlated from one studied well to the adjacent wells in the same gas field.

Without wishing to be bound by theory, it is believed that the methods can allow for the identification of regional and/or global events associated with the deposition and accumulation of relatively large amounts of organic matter (e.g., oceanic anoxic events, described in more detail below). Thus, the methods of the disclosure can identify relatively large deposits of organic matter with fewer measurements of multiple wells and/or outcrops relative to certain other methods of identifying deposits or organic matter. Furthermore, the methods can reduce time and/or costs associated with the measurement of samples to determine the location of source rocks relative to certain other methods of identifying the location of source rocks as measurements from various wells and/or outcrops can be reduced.

In a first aspect, the disclosure provides a method of determining a depth source rocks within a formation, the method including; measuring a carbon isotope ratio and an oxygen isotope ratio from samples taken from a formation at a plurality of depths within the formation; generating a data set including: i) the measured carbon isotope ratio versus the depth of the formation; and ii) the measured oxygen isotope ratio versus the depth of the formation; and using the data set to determine a depth of the source rocks within the formation.

In some embodiments, using the data set to determine the depth of the source rocks within the formation includes identifying a positive shift in the measured carbon isotope ratio followed by a local maximum value in the measured carbon isotope ratio as the depth decreases. The local maximum value in the measured carbon isotope ratio as the depth decreases corresponds to the depth of the source rocks.

In some embodiments, a first negative shift in the measured carbon isotope ratio occurs after the local maximum in the measured carbon isotope ratio as the depth decreases.

In some embodiments, a second negative shift in the measured carbon isotope ratio occurs before the positive shift in the measured carbon isotope ratio as the depth decreases.

In some embodiments, using the data set to determine the depth of the source rocks in the formation further includes identifying, as the depth within the formation decreases, a negative shift in the measured oxygen isotope ratio followed by a period of relatively consistent value in the measured oxygen isotope ratio. The negative shift in the measured oxygen isotope ratio occurs at a depth within the formation corresponding to the positive shift in the measured carbon isotope ratio as the depth decreases and the period of relatively consistent value in the measured oxygen isotope ratio occurs at a depth corresponding to the local maximum in the measured carbon isotope ratio as the depth decreases.

In some embodiments, a positive shift occurs after the period of relatively consistent value in the measured oxygen isotope ratio as the depth decreases. The positive shift in the measured oxygen isotope ratio occurs at a depth correspond to the first negative shift in the measured carbon isotope ratio as the depth decreases.

In some embodiments, using the data set to determine the depth of the source rocks in the formation includes identifying, as the depth within the formation decreases, a negative shift in the measured oxygen isotope ratio followed by a period of relatively consistent value in the measured oxygen isotope ratio.

In some embodiments, a positive shift occurs after the period of relatively consistent value in the measured oxygen isotope ratio as the depth decreases.

In some embodiments, the method further includes measuring a strontium isotope ratio of the samples, and the data set further includes the measured strontium isotope ratio versus depth of the formation.

In some embodiments, the method further includes measuring redox sensitive element content of the samples, and the data set further includes the measured redox sensitive element content versus depth of the formation.

In some embodiments, the method further includes measuring a carbonate content of the samples, and the data set further includes the measured carbonate content versus depth of the formation.

In some embodiments, the method further includes measuring a elastic content of the samples, and the data set further includes the measured elastic content versus depth of the formation.

In some embodiments, the method further includes producing a hydrocarbon from the depth determined using the data set.

In a second aspect, the disclosure provides one or more machine-readable hardware storage devices including instructions that are executable by one or more processing devices to perform operations including a method of the disclosure.

In a third aspect, the disclosure provides, a system, including one or more processing devices, and one or more machine-readable hardware storage devices including instructions that are executable by the one or more processing devices to perform operations including a method of the disclosure.

In a fourth aspect, the disclosure provides a method of determining a depth of source rocks within a formation, the method including: measuring a carbon isotope ratio from samples taken at a plurality of depths from a formation; generating a data set including the carbon isotope ratio versus depth; and using the data set to determine a depth of the source rocks within the formation.

In some embodiments, using the data set to determine the depth of the source rocks within the formation includes identifying a positive shift in the measured carbon isotope ratio followed by a local maximum value in the measured carbon isotope ratio as the depth decreases.

The local maximum value in the measured carbon isotope ratio as the depth decreases corresponds to the depth of the source rocks.

In some embodiments, a negative shift in the measured carbon isotope ratio occurs after the local maximum in the measured carbon isotope ratio as the depth decreases.

In some embodiments, a negative shift in the measured carbon isotope ratio occurs before the positive shift in the measured carbon isotope ratio as the depth decreases.

In a fifth aspect, the disclosure provides one or more machine-readable hardware storage devices including instructions that are executable by one or more processing devices to perform operations including a method of the disclosure.

In a sixth aspect, the disclosure provides a system, including one or more processing devices, and one or more machine-readable hardware storage devices including instructions that are executable by the one or more processing devices to perform operations including a method of the disclosure.

DETAILED DESCRIPTION

Methods Using Carbon and/or Oxygen Isotope Ratios

Figures 1A, 1B, 1C:
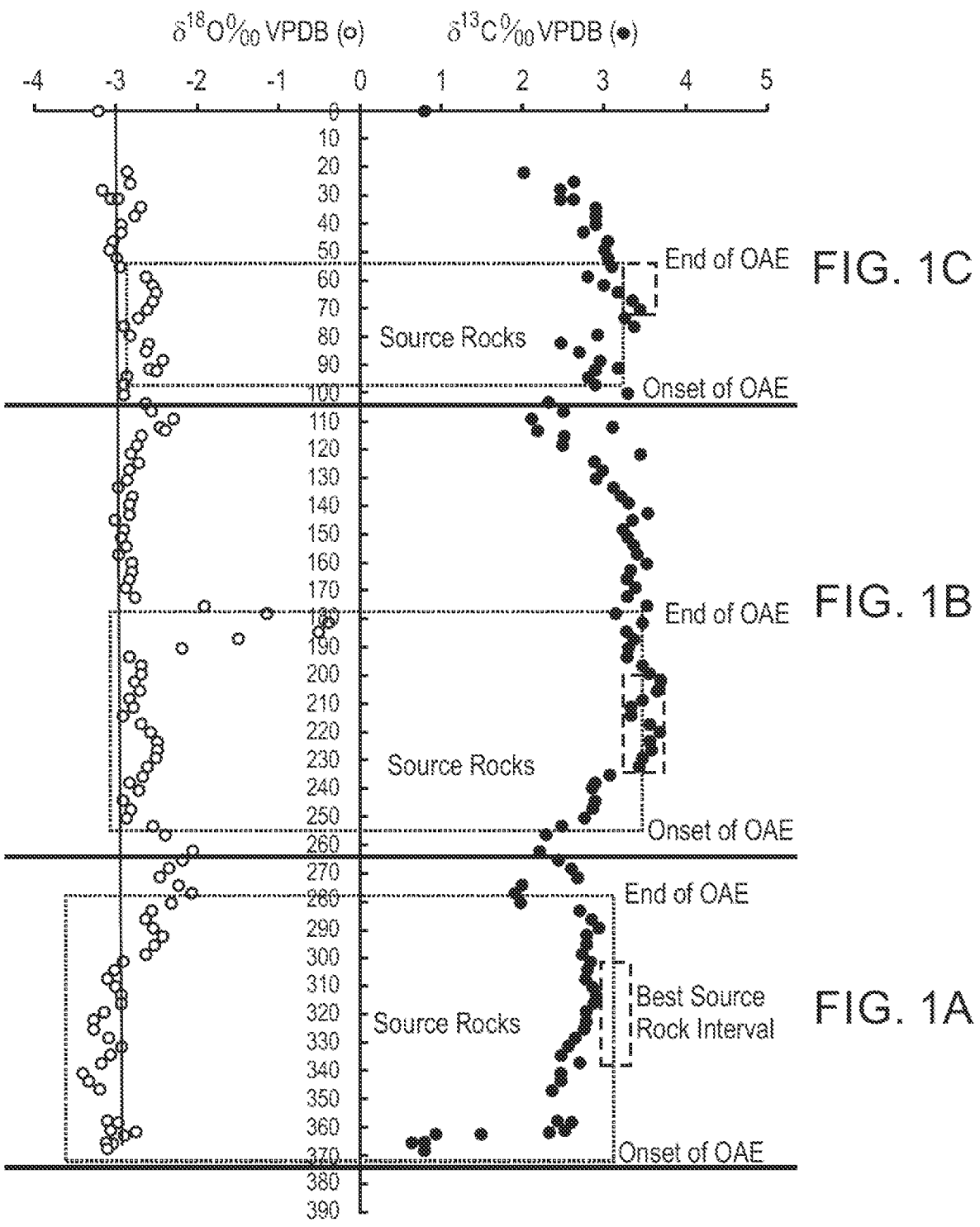
FIG. 1A depicts a plot of carbon and oxygen isotope ratios versus depth in a formation.
FIG. 1B depicts a plot of carbon and oxygen isotope ratios versus depth in a formation.
FIG. 1C depicts a plot of carbon and oxygen isotope ratios versus depth in a formation.

FIGS. 1A-1C depict plots of carbon and oxygen isotope ratios ($\delta^{13}C$ ‰ VPDB and $\delta^{18}O$ ‰ VPDB, respectively) of carbonate samples versus depth in three formations. The carbon and oxygen isotope ratio values were obtained from carbonate samples taken from the formation at different depths from the surface. The minimum depth shown was set to 0. Details regarding the construction of FIGS. 1A-1C are provided below. Without wishing to be bound by theory, it is believed that certain patterns in the carbon and/or oxygen isotope ratios versus depth (described in the next paragraph) can indicate the presence of source rocks and regions with relatively high TOC in the formation.

In each of FIGS. 1A-1C, as the depth decreases (moving towards the surface, starting from the bottom of the plot and moving up) the value of the carbon isotope ratio undergoes a short negative shift followed by a large positive shift. In other words, when moving towards the surface, the value of the carbon isotope ratio decreases and then greatly increases. As the depth continues to decrease, the carbon isotope ratio reaches a maximum value, then decreases again (final negative shift). Without wishing to be bound by theory, it is believed that such a pattern in the carbon isotope ratio versus depth indicates the presence of source rocks and relatively high TOC at the depth that corresponds to the maximum value of the carbon isotope ratio (desirable interval). However, in some embodiments, the final negative shift in the carbon isotope ratio is not present.

In FIGS. 1A-1C, source rocks are expected to be within the depth interval indicated by the dotted lines and the best source rocks with the highest TOC are expected be in the depth interval indicated by the dashed lines, which corresponds to the maximum value of the carbon isotope ratio. The interval indicated by the dashed rectangle is therefore expected to be the highest production zone in each of the formations. Without wishing to be bound by theory, it is believed that the depth interval indicated by the dotted lines in FIGS. 1A-1C corresponds to a period in geological time during which an oceanic anoxic events (OAE) event occurred (see discussion below).

In FIGS. 1A-1C, as the depth decreases (moving towards the surface, starting from the bottom of the plot and moving up) the value of the oxygen isotope ratio exhibits a negative shift followed by a relatively consistent value, then a positive shift in its value. The negative shift of the oxygen isotope ratio occurs at the same depth as the positive shift of the carbon isotope ratio. Additionally, the range of depth of relatively consistent value of the oxygen isotope ratio occurs at the same range of depth as the maximum value of the carbon isotope ratio. Further, the positive shift of the oxygen isotope ratio occurs at the same depth as the negative shift of the carbon isotope ratio after its maximum value.

In FIGS. 1A-1C, the source rocks are expected be in the depth interval of relatively consistent value of the oxygen isotope ratio. Without wishing to be bound by theory, it is believed that the depth interval indicated by the dotted lines in FIGS. 1A-1C corresponds to a period in geological time during climate warming occurred and the warm climate was maintained (see discussion below).

Without wishing to be bound by theory, it is believed that the patterns in the carbon and oxygen isotope ratios described above may be due to an event associated with the deposition and accumulation of relatively large amounts of organic matter, such as an anoxic event, dysoxic-anoxic event, and dysoxic event. It is further believed that such an event occurs regionally or globally, thus reducing the need for measurements of samples from different wells and/or outcrops as measurements can be extrapolated across different formations, thereby allowing data retrieved from a given formation to be used as the basis for predicting the depth of source rocks and regions with relatively high TOC in other formations (e.g., adjacent formations, formations in other locations). Without wishing to be bound, by theory, it is believed that based on the shifts in the isotope ratios, the events in the formations of FIGS. 1A-1C are expected to be an anoxic event, a dysoxic-anoxic event, and a dysoxic event, respectively.

Without wishing to be bound by theory, it is believed that a negative oxygen isotope excursion results from climate warming, whereas a negative carbon isotope excursion is a result of $^{12}C$ deficiency in carbonates due to the deposition/ accumulation of $^{12}C$-enriched organic matter in an anoxic environment.

Without wishing to be bound by theory, it is believed that the intensity ($\delta^{13}C$ ‰ and $\delta^{18}O$ ‰ isotope ratio values) and depth of the excursions depends on the geological conditions that gave rise to the excursions. Without wishing to be bound by theory, it is believed that the scale of the shift in the isotope ratio and/or the depth over which the shift extends can determine the extent (e.g., local, regional, global) of the event and properties (e.g., thickness, content of organic matter) of the hydrocarbon deposit. For example, the thickness depends on the depositional rate. A relatively slow rate will usually produce a thinner hydrocarbon deposit. A larger shift generally suggests a higher potential. The formation of FIG. 1A is expected to have has the highest potential and the formation of FIG. 1C is expected to have the lowest potential. The shift in the isotope ratio and/or the depth over which the shift extends can also determine the occurrence of a global ocean anoxic event (relatively large scale and relatively large accumulation of organic matter), a global oceanic dysoxic event (relatively large scale event with a relatively low quality organic matter), or a local basinal anoxic event (relatively small scale and relatively high quality organic matter). In general, a carbon isotope ratio shift of more than 2‰ plus an associated oxygen isotope shift may correspond to an OAE. In general, dysoxic-anoxic events can be difficult to quantify but may correspond to a shift of 1-2‰ in the carbon isotope ratio value.

Without wishing to be bound by theory, it is believed that over the course of the Earth's history, the Earth experienced relatively high temperatures/global warming due to the release of greenhouse gases such as carbon dioxide and methane into the atmosphere, leading to oceanic anoxic events (OAEs) from deep oceanic to shelf basins and platforms. Without wishing to be bound by theory, it is believed that past OAEs are associated with relatively large accumulation and preservation of organic matter, thus marine sediments deposited during an OAF can be major petroleum source rocks. Furthermore, it is believed that such source rocks are usually formed regionally and/or globally rather than locally.

Without wishing to be bound by theory, it is believed that the patterns in the oxygen and carbon isotope ratios versus depth indicate climate change from a colder to warmer climate and the climate remaining warm. Climate change can cause changes in the carbon isotope ratios (due to organic matter cycling) and oxygen isotope ratios (due to temperature fluctuation). For example, in the formation of FIG. 1B, starting at the bottom of the plot, the oxygen isotope ratio has a relatively quick negative shift to lower values, and remains at that value for a while, and then the value increases to form a cycle (dotted box). For OAE, global warming occurred relatively quickly, which is why the negative shift in the oxygen isotope ratio value near the bottom of the plot is relatively short. Then the Earth stayed warm for a while, so not much change occurred in the oxygen isotope ratios. During this warm period, carbon dioxide levels were relatively high, plants (e.g., trees) underwent major growth and gradually consumed carbon dioxide. Eventually, the temperature and carbon dioxide content dropped, and the oxygen isotope ratio increased, thereby forming a warming up to cooling down cycle. During global warming, sea levels rise and marine life undergoes major growth as nutrients enter the seas from land due to weathering. Organic matter associated with living matter gradually accumulates in deeper parts of oceanic floors, changing the organic carbon balance. In general, $^{12}C$ is preferred in organic carbon, so the non-organic matter (carbonates) would be depleted in $^{12}C$ and enriched by $^{13}C$, resulting in a positive shift in the carbon isotope ratio value. The accumulation of organic matter is relatively slow, hence the positive carbon isotope excursion lasts longer.

Without wishing to be bound by theory, it is believed that oxygen isotope ratios can be modified by rock diagenetic processes, while carbon isotope ratios harder to modify relative to the oxygen isotope ratios.

Without wishing to be bound by theory, it is believed that in some embodiments, an OAE source rock will have a carbon and oxygen isotope pattern as shown in FIGS. 1A-1C.

Without wishing to be bound by theory, it is believed that the lack of a carbon and/or oxygen isotope ratio excursions versus depth may indicate that the formation does not include a source rock or an interval with high TOC.

Figure 2:
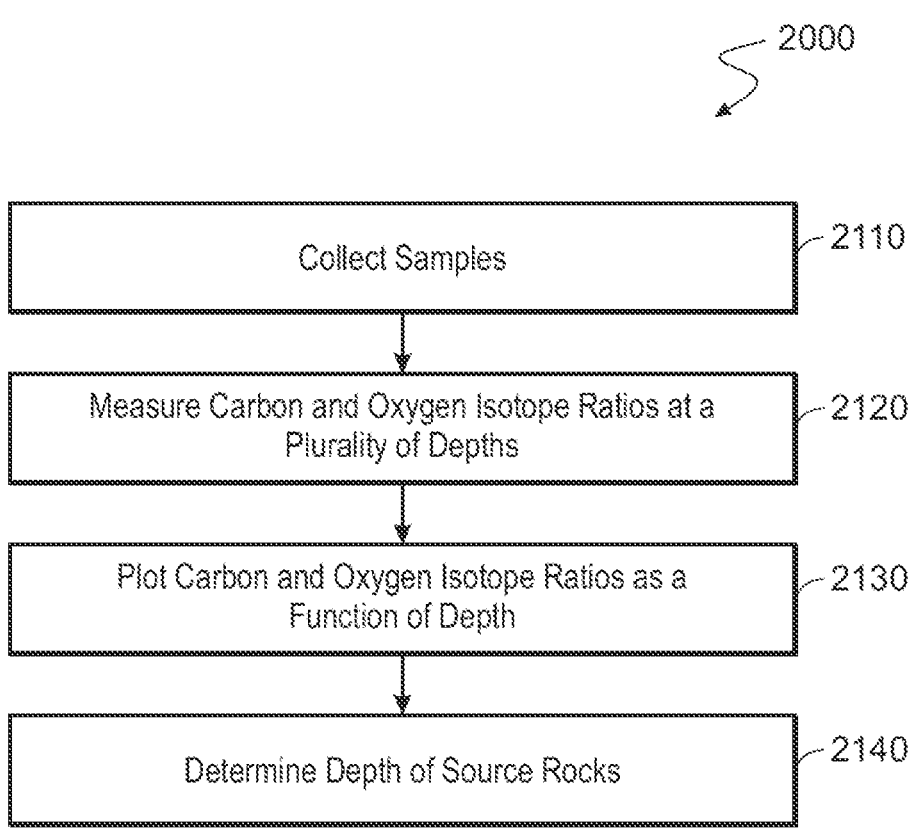
FIG. 2 depicts a flowchart for a method.

FIG. 2 depicts a flowchart for a method 2000 for identifying the depth of source rocks and regions with high TOC in a formation.

In step 2110, carbonate samples are collected from the formation at a plurality of depths. Generally, the formation is a carbonate formation or includes carbonates. In the formation, the carbonate component should be a primary deposit instead of late cements, the carbonate component should be continuous, so a continuous isotope profile can be established, and no significant diagenesis should have occurred.

In step 2120, the carbon and oxygen isotope ratios in the carbonate samples are measured. In general, the carbon and oxygen isotope ratios can be determined using any suitable method. In certain embodiments, carbon and oxygen isotope ratios are determined using isotope ratio mass spectrometry with appropriate standards.

The carbon isotope ratio can be calculated using the equation:

$$\delta^{13}C = \left( \frac{\left(^{13}C/^{12}C\right)_{sample}}{\left(^{13}C/^{12}C\right)_{standard}} - 1 \right) \times 1000 \, 0/00$$

Similarly, the oxygen isotope ratio can be calculated using the equation:

$$\delta^{18}O = \left( \frac{\left(^{18}O/^{16}O\right)_{sample}}{\left(^{18}O/^{16}O\right)_{standard}} - 1 \right) \times 1000 \, 0/00$$

In step 2130, the carbon and oxygen isotope ratios are plotted versus depth. Such plots are depicted in FIGS. 1A-1C.

In step 2140, the plot generated in the step 2130 is used to determine the location (e.g., depth) of source rocks in the formation. This is achieved by identifying the patterns in the carbon and/or oxygen isotope ratio values versus depth described above and the depth that corresponds to the maximum value of the carbon isotope ratio.

The samples collected in step 2110 measured in step 2120 include carbonate samples (e.g., cored carbonate rocks, outcrop carbonate rocks) from a carbonate formation. Powder samples are then obtained (e.g., using a drill to drill into a sample of the cored carbonate rock or the outcrop carbonate rock). In some embodiments, the samples are from core samples. Without wishing to be bound by theory, it is believed that, when making the isotope measurements, more representative results are achieved using powdered rock samples, and that, as a result, cements, elastic fragments and fossils should be avoided when making the isotope measurements.

Generally, the depths of the formation that are investigated depends on local geological conditions. In general, the interval between samples may be selected based on the depositional environment of the source rock. In some embodiments, the interval between samples is at least 0.3 (e.g., at least 0.5, at least 1, at least 1.5, at least 2, at least 2.5, at least 3, at least 3.5, at least 4, at least 4.5, at least 5, at least 5.5, at least 6, at least 6.5, at least 7, at least 7.5, at least 8, at least 8.5, at least 9, at least 9.5) meters and/or at most 10 (e.g., at most 9.5, at most 9, at most 8.5, at most 8, at most 7.5, at most 7, at most 6.5, at most 6, at most 5.5, at most 5, at most 4.5, at most 4, at most 3.5, at most 3, at most 2.5, at most 2, at most 1.5, at most 1, at most 0.5) meters. In some embodiments, the interval between samples is 0.3 meters. In some embodiments, the interval between samples is 0.9 meters. In general, the interval between samples 1 is meter or less.

In general, the sampling interval depends on targeted thickness. For example, source rock or black shale with high TOC are usually relatively thin, e.g., only 10 m, so a relatively small sampling interval, such as 0.3 in may be used. For a thicker formation with lower TOC, e.g., 200 m or more, a larger sampling interval, such as 1 m, may be used.

Generally, the sampling interval depends on presence of changes in rocks, such as the changes in fossils, lithology, and rock texture. A sample may be taken at the spot with a change, and samples within this region can be taken at a sampling interval of 0.1 in to 10 m, taking into consideration the total studied thickness.

Without wishing to be bound by theory, it is believed that increasing the total number of samples (denser sampling) over the formation can yield higher resolution. If the targeted formation is relatively large and the location of the OAE is not known, a first scan with a relatively large sampling interval can be used to reduce work and cost. After the initial scan, a detailed sampling using a smaller sampling interval in a portion of the formation section may be conducted.

In general, the amount of TOC in the sweet spot is a relative number and depends on the geographical location.

Data obtained from the measurements, such as carbon and/or oxygen isotope ratio information versus depth, can be in the form of a data set. The data set can be used to generate the plots and/or identify the desirable intervals.

In general, the trends in the carbon and oxygen isotope pattern versus depth can be determined by visual inspection of the plots (e.g., FIGS. 1A-1C) and/or using an appropriate algorithm.

Computational Operations

Figure 3:
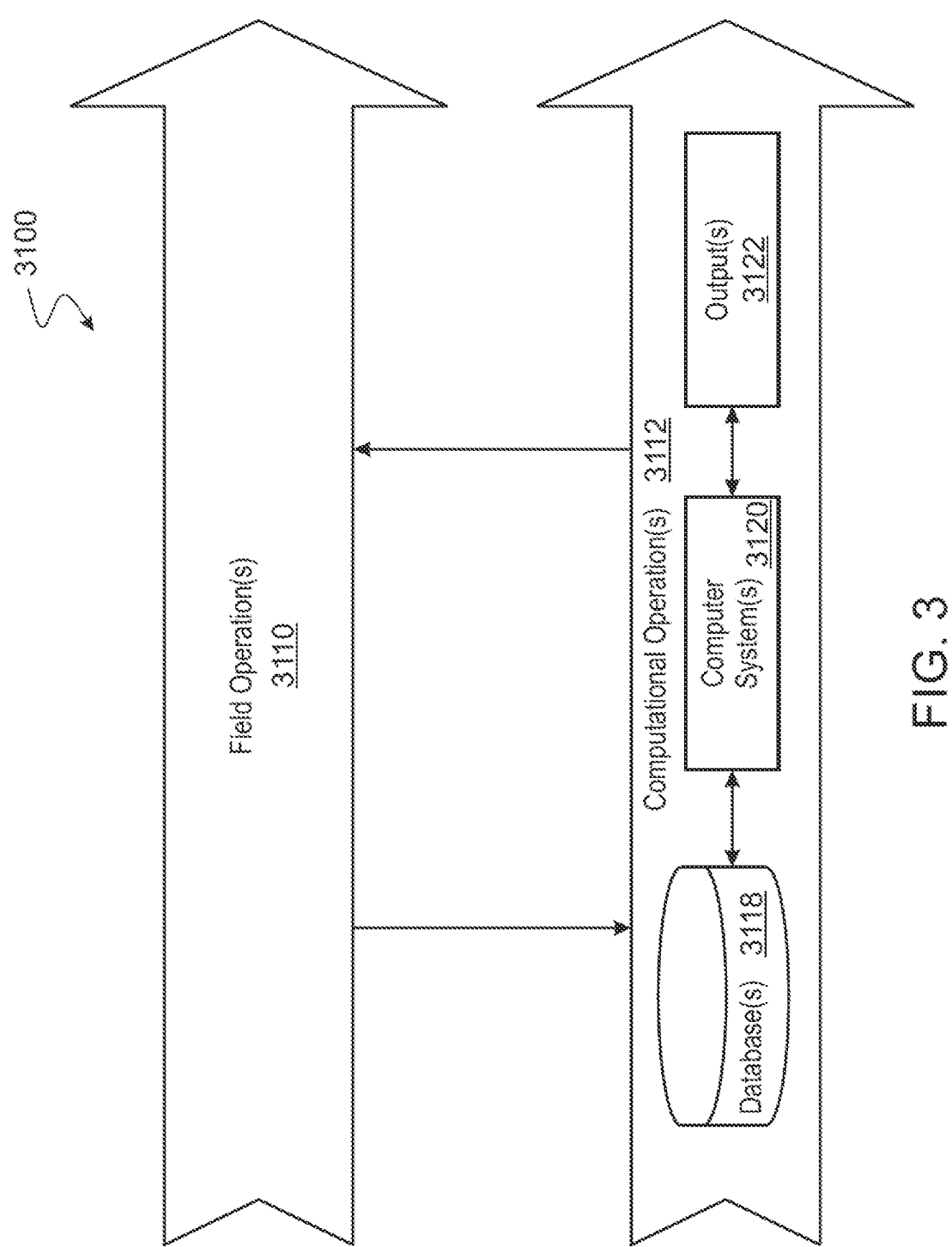
FIG. 3 depicts a schematic of hydrocarbon production operations.

FIG. 3 illustrates hydrocarbon production operations 3100 that include both one or more field operations 3110 and one or more computational operations 3112, which exchange information and control exploration for the production of hydrocarbons. In some implementations, outputs of techniques of the present disclosure can be performed before, during, or in combination with the hydrocarbon production operations 3100, specifically, for example, either as field operations 3110 or computational operations 3112, or both. Examples of field operations 3110 include forming/drilling a wellbore, hydraulic fracturing, producing through the wellbore, injecting fluids (such as water) through the wellbore, to name a few. In some implementations, methods of the present disclosure can trigger or control the field operations 3110. For example, the methods of the present disclosure can generate data from hardware/software including sensors and physical data gathering equipment (e.g., seismic sensors, well logging tools, flow meters, and temperature and pressure sensors). The methods of the present disclosure can include transmitting the data from the hardware/software to the field operations 3110 and responsively triggering the field operations 3110 including, for example, generating plans and signals that provide feedback to and control physical components of the field operations 3110. Alternatively or in addition, the field operations 3110 can trigger the methods of the present disclosure. For example, implementing physical components (including, for example, hardware, such as sensors) deployed in the field operations 3110 can generate plans and signals that can be provided as input or feedback (or both) to the methods of the present disclosure.

Examples of computational operations 3112 include one or more computer systems 3120 that include one or more processors and computer-readable media (e.g., non-transitory computer-readable media) operatively coupled to the one or more processors to execute computer operations to perform the methods of the present disclosure. The computational operations 3112 can be implemented using one or more databases 3118, which store data received from the field operations 3110 and/or generated internally within the computational operations 3112 (e.g., by implementing the methods of the present disclosure) or both. For example, the one or more computer systems 3120 process inputs from the field operations 3110 to assess conditions in the physical world, the outputs of which are stored in the databases 3118. For example, seismic sensors of the field operations 3110 can be used to perform a seismic survey to map subterranean features, such as facies and faults. In performing a seismic survey, seismic sources (e.g., seismic vibrators or explosions) generate seismic waves that propagate in the earth and seismic receivers (e.g., geophones) measure reflections generated as the seismic waves interact with boundaries between layers of a subsurface formation. The source and received signals are provided to the computational operations 3112 where they are stored in the databases 3118 and analyzed by the one or more computer systems 3120.

In some implementations, one or more outputs 3122 generated by the one or more computer systems 3120 can be provided as feedback/input to the field operations 3110 (either as direct input or stored in the databases 3118). The field operations 3110 can use the feedback/input to control physical components used to perform the field operations 3110 in the real world.

For example, the computational operations 3112 can process the seismic data to generate three-dimensional (3D) maps of the subsurface formation. The computational operations 3112 can use these 3D maps to provide plans for locating and drilling exploratory wells. In some operations, the exploratory wells are drilled using logging-while-drilling (LWD) techniques which incorporate logging tools into the drill string. LWD techniques can enable the computational operations 3112 to process new information about the formation and control the drilling to adjust to the observed conditions in real-time.

The one or more computer systems 3120 can update the 3D maps of the subsurface formation as information from one exploration well is received and the computational operations 3112 can adjust the location of the next exploration well based on the updated 3D maps. Similarly, the data received from production operations can be used by the computational operations 3112 to control components of the production operations. For example, production well and pipeline data can be analyzed to predict slugging in pipelines leading to a refinery and the computational operations 3112 can control machine operated valves upstream of the refinery to reduce the likelihood of plant disruptions that run the risk of taking the plant offline.

In some implementations of the computational operations 3112, customized user interfaces can present intermediate or final results of the above-described processes to a user. Information can be presented in one or more textual, tabular, or graphical formats, such as through a dashboard. The information can be presented at one or more on-site locations (such as at an oil well or other facility), on the Internet (such as on a webpage), on a mobile application (or app), or at a central processing facility.

The presented information can include feedback, such as changes in parameters or processing inputs, that the user can select to improve a production environment, such as in the exploration, production, and/or testing of petrochemical processes or facilities. For example, the feedback can include parameters that, when selected by the user, can cause a change to, or an improvement in, drilling parameters (including drill bit speed and direction) or overall production of a gas or oil well. The feedback, when implemented by the user, can improve the speed and accuracy of calculations, streamline processes, improve models, and solve problems related to efficiency, performance, safety, reliability, costs, downtime, and the need for human interaction.

In some implementations, the feedback can be implemented in real-time, such as to provide an immediate or near-immediate change in operations or in a model. The term real-time (or similar terms as understood by one of ordinary skill in the art) means that an action and a response are temporally proximate such that an individual perceives the action and the response occurring substantially simultaneously. For example, the time difference for a response to display (or for an initiation of a display) of data following the individual's action to access the data can be less than 1 millisecond (ms), less than 1 second (s), or less than 5 s. While the requested data need not be displayed (or initiated for display) instantaneously, it is displayed (or initiated for display) without any intentional delay, taking into account processing limitations of a described computing system and time required to, for example, gather, accurately measure, analyze, process, store, or transmit the data.

Events can include readings or measurements captured by downhole equipment such as sensors, pumps, bottom hole assemblies, or other equipment. The readings or measurements can be analyzed at the surface, such as by using applications that can include modeling applications and machine learning. The analysis can be used to generate changes to settings of downhole equipment, such as drilling equipment. In some implementations, values of parameters or other variables that are determined can be used automatically (such as through using rules) to implement changes in oil or gas well exploration, production/drilling, or testing. For example, outputs of the present disclosure can be used as inputs to other equipment and/or systems at a facility. This can be especially useful for systems or various pieces of equipment that are located several meters or several miles apart, or are located in different countries or other jurisdictions.

Additional Measurements

In certain embodiments, a method of the disclosure can further include studying the general mineral composition using an appropriate technique such as XRD or staining. For example, staining can be used to differentiate dolomite from aragonite and calcite. Alizarin red S and potassium ferricyanide dissolved in a dilute hydrochloric acid (1%) solution can stain the more reactive calcite and aragonite red while the less reactive dolomite remains unstained. In some embodiments, slabs or thin sections made from representative lithology are placed in the stain solution at 25° C. for 1-2 minutes. XRD can also provide the mineral composition. Without wishing to be bound by theory, it is believed that studying the general mineral composition can provide relatively quick information regarding mineral composition and depositional and diagenetic environments.

In some embodiments, in addition to carbon and/or oxygen isotope ratios, one or more additional geochemical parameters can be used to identify source rocks. The additional geochemical parameters can include strontium isotope ratios ($^{87}Sr/^{86}Sr$), redox sensitive element content, carbonate content and clastic content. Without wishing to be bound by theory, it is believed that the presence of these geochemical parameters indicates the occurrence of an OAE, thereby suggesting the presence of source rocks.

In general the strontium isotope ratio can be measured using any appropriate technique such as mass spectrometry with standards for calibration. Without wishing to be bound by theory, it is believed that elevated strontium isotope ratio values may have arisen from sea level rise and intensive land weathering with a warming climate. Additionally, it is believed that the strontium isotope ratios can vary considerably over geological time.

Without wishing to be bound by theory, it is believed that a relatively high elastic content (e.g., clay, quartz, feldspars) and/or a relatively low carbonate content suggests more continental contribution from increasing weathering of land causing the transfer of nutrients and elastic minerals to the ocean. Additionally, it is believed that a plot of the elastic content versus depth can show spikes or outstanding values to indicate the presence of source rocks.

Without wishing to be bound by theory, it is believed that a relatively high content of redox sensitive elements, such as Cr, Co, and/or Ni, suggests an anoxic environment. Additionally, it is believed that a plot of the redox sensitive element content versus depth can show spikes or outstanding values to indicate the presence of source rocks.

Example

Cored carbonate samples were collected at intervals of 20, 30 and 40 feet in the formations of FIGS. 1A, 1B and 1C, respectively. A dental drill was used to drill into the samples to obtain powder samples while avoiding cements, elastic fragments and fossils. Large grains, if present, were ground to a homogenous powder using a mortar and pestle.

Powdered samples were placed in 10 mL vials and dried in an oven at 50 overnight. Carbon and oxygen isotope ratios of the samples were measured using a Thermo-Fisher Gas-Bench isotope-ratio mass spectrometry (IRMS) instrument. 300 μg of sample was weighed and placed into vials and the vials were capped with a septum. The vials were vacuumed and 4 drops (400 µg) concentrated phosphoric acid was added to produce carbon dioxide gas. The carbon dioxide gas was measured on the IRMS instrument to measure carbon and oxygen isotope ratios simultaneously. Standards were used to calibrate the carbon and isotopes of samples and confirm the accuracy and precision of the measurements.

The carbon and oxygen isotope ratios versus depth (in feet) were then plotted using Excel and presented in FIGS. 1A-1C and carbon and oxygen isotope ratio excursions were identified. The minimum depth shown was set to 0. The carbon isotope ratios are shown with black circles and the oxygen isotope ratios are shown with white circles.

For each formation, as the depth decreased (moving towards the surface) the carbon isotope ratio began at a negative shift, and then the value had a long positive increase. After the carbon isotope ratio peaked, the ratio value slightly decreased. For the oxygen isotope ratios, as the depth decreased, the oxygen isotope ratios also started with a negative shift in value aligned with the carbon isotope shift. Following the negative shift, the oxygen isotope ratio remained relatively consistent before experiencing a slightly positive shift in value. The oxygen and carbon shifts in value are related. The initial to final shifts indicate an OAE and potential source rocks. The initial negative shift in the carbon isotope ratio would be easier to see with more samples.

Without wishing to be bound by theory, it is believed that source rocks are expected to be within the whole interval starting from the negative C-isotope shift and positive O-isotope shift through the long positive carbon isotope excursion, potentially even to the end of the slight C-isotope excursion (dotted lines). However, the best source rocks with the highest TOC are expected be around the peak (most positive portion) of the positive carbon isotope ratio excursion (dashed lines), which is expected to be the highest production zones. These regions (dashed lines) may also have relatively high porosity due to TOC cracking.

The best interval in the source rock is around the carbon isotope ratio peak (maximum value) in the pattern described above. Formation A has the largest isotope shift of the three formations, indicating the best signal for OAE and therefore the best source rock. Conversely, formation C is expected to have the worst source rocks.

Embodiments

1. A method of determining a depth of source rocks within a formation, the method including:
   measuring a carbon isotope ratio and an oxygen isotope ratio from samples taken from a formation at a plurality of depths within the formation;
   generating a data set including: i) the measured carbon isotope ratio versus the depth of the formation; and ii) the measured oxygen isotope ratio versus the depth of the formation; and
   using the data set to determine a depth of the source rocks within the formation.
2. The method of embodiment 1, wherein using the data set to determine the depth of the source rocks within the formation includes:
   identifying a positive shift in the measured carbon isotope ratio followed by a local maximum value in the measured carbon isotope ratio as the depth decreases, wherein the local maximum value in the measured carbon isotope ratio as the depth decreases corresponds to the depth of the source rocks.
3. The method of embodiment 2, wherein a first negative shift in the measured carbon isotope ratio occurs after the local maximum in the measured carbon isotope ratio as the depth decreases.
4. The method of embodiment 3, wherein a second negative shift in the measured carbon isotope ratio occurs before the positive shift in the measured carbon isotope ratio as the depth decreases.
5. The method of any one of embodiments 2-4, wherein using the data set to determine the depth of the source rocks in the formation further includes:
   identifying, as the depth within the formation decreases, a negative shift in the measured oxygen isotope ratio followed by a period of relatively consistent value in the measured oxygen isotope ratio,
   wherein:
      the negative shift in the measured oxygen isotope ratio occurs at a depth within the formation corresponding to the positive shift in the measured carbon isotope ratio as the depth decreases; and
      the period of relatively consistent value in the measured oxygen isotope ratio occurs at a depth corresponding to the local maximum in the measured carbon isotope ratio as the depth decreases.
6. The method of embodiment 5, wherein:
   a positive shift occurs after the period of relatively consistent value in the measured oxygen isotope ratio as the depth decreases; and
   wherein the positive shift in the measured oxygen isotope ratio occurs at a depth correspond to the first negative shift in the measured carbon isotope ratio as the depth decreases.
7. The method of embodiment 1, wherein using the data set to determine the depth of the source rocks in the formation includes:
   identifying, as the depth within the formation decreases, a negative shift in the measured oxygen isotope ratio followed by a period of relatively consistent value in the measured oxygen isotope ratio.
8. The method of embodiment 7, wherein:
   a positive shift occurs after the period of relatively consistent value in the measured oxygen isotope ratio as the depth decreases.
9. The method of any one of embodiments 1-8, wherein:
   the method further includes measuring a strontium isotope ratio of the samples; and
   the data set further includes the measured strontium isotope ratio versus depth of the formation.
10. The method of any one of embodiments 1-9, wherein:
   the method further includes measuring redox sensitive element content of the samples; and
   the data set further includes the measured redox sensitive element content versus depth of the formation.
11. The method of any one of embodiments 1-10, wherein:
   the method further includes measuring a carbonate content of the samples; and
   the data set further includes the measured carbonate content versus depth of the formation.
12. The method of any one of embodiments 1-11, wherein:

the method further includes measuring a elastic content of the samples; and the data set further includes the measured elastic content versus depth of the formation.

13. One or more machine-readable hardware storage devices including instructions that are executable by one or more processing devices to perform operations including the method any one of embodiments 1-12.

14. A system including:

one or more processing devices; and one or more machine-readable hardware storage devices including instructions that are executable by the one or more processing devices to perform operations including the method of any one of embodiments 1-12.

15. A method of determining a depth of source rocks within a formation, the method including:

measuring a carbon isotope ratio from samples taken at a plurality of depths from a formation;

generating a data set including the carbon isotope ratio versus depth; and using the data set to determine a depth of the source rocks within the formations 16. The method of embodiment 15, wherein using the data set to determine the depth of the source rocks within the formation includes:

identifying a positive shift in the measured carbon isotope ratio followed by a local maximum value in the measured carbon isotope ratio as the depth decreases, wherein the local maximum value in the measured carbon isotope ratio as the depth decreases corresponds to the depth of the source rocks.

17. The method of embodiment 16, wherein a negative shift in the measured carbon isotope ratio occurs after the local maximum in the measured carbon isotope ratio as the depth decreases.

18. The method of embodiment 17, wherein a negative shift in the measured carbon isotope ratio occurs before the positive shift in the measured carbon isotope ratio as the depth decreases.

19. One or more machine-readable hardware storage devices including instructions that are executable by one or more processing devices to perform operations including the method of any one of embodiments 15-18.

20. A system including:

one or more processing devices; and one or more machine-readable hardware storage devices including instructions that are executable by the one or more processing devices to perform operations including the method of any one of embodiments 15-18.

21. The method of any one of embodiments 1-12 and 15-18, further including, producing a hydrocarbon from the depth determined using the data set.

What is claimed:

1. A method of determining a depth of source rocks within a formation, the method comprising:

measuring a carbon isotope ratio and an oxygen isotope ratio from samples taken from a formation at a plurality of depths within the formation;

generating a data set comprising: i) the measured carbon isotope ratio versus the depth of the formation; and ii) the measured oxygen isotope ratio versus the depth of the formation; and using the data set to determine a depth of the source rocks within the formation;

wherein using the data set to determine the depth of the source rocks in the formation comprises:

identifying a positive shift in the measured carbon isotope ratio followed by a local maximum value in the measured carbon isotope ratio as the depth decreases, wherein the local maximum value in the measured carbon isotope ratio as the depth decreases corresponds to the depth of the source rocks.

2. The method of claim 1, wherein a first negative shift in the measured carbon isotope ratio occurs after the local maximum in the measured carbon isotope ratio as the depth decreases.

3. The method of claim 2, wherein a second negative shift in the measured carbon isotope ratio occurs before the positive shift in the measured carbon isotope ratio as the depth decreases.

4. The method of claim 1, wherein using the data set to determine the depth of the source rocks within the formation further comprises:

identifying, as the depth within the formation decreases, a negative shift in the measured oxygen isotope ratio followed by a period of relatively consistent value in the measured oxygen isotope ratio, wherein:

the negative shift in the measured oxygen isotope ratio occurs at a depth within the formation corresponding to the positive shift in the measured carbon isotope ratio as the depth decreases; and the period of relatively consistent value in the measured oxygen isotope ratio occurs at a depth corresponding to the local maximum in the measured carbon isotope ratio as the depth decreases.

5. The method of claim 4, wherein:

a positive shift occurs after the period of relatively consistent value in the measured oxygen isotope ratio as the depth decreases; and wherein the positive shift in the measured oxygen isotope ratio occurs at a depth correspond to the first negative shift in the measured carbon isotope ratio as the depth decreases.

6. The method of claim 1, wherein using the data set to determine the depth of the source rocks within the formation further comprises:

identifying, as the depth within the formation decreases, a negative shift in the measured oxygen isotope ratio followed by a period of relatively consistent value in the measured oxygen isotope ratio.

7. The method of claim 6, wherein:

a positive shift occurs after the period of relatively consistent value in the measured oxygen isotope ratio as the depth decreases.

8. The method of claim 1, wherein:

the method further comprises measuring a strontium isotope ratio of the samples; and the data set further comprises the measured strontium isotope ratio versus depth of the formation.

9. The method of claim 1, wherein:

the method further comprises measuring redox sensitive element content of the samples; and the data set further comprises the measured redox sensitive element content versus depth of the formation.

10. The method of claim 1, wherein:

the method further comprises measuring a carbonate content of the samples; and the data set further comprises the measured carbonate content versus depth of the formation.

11. The method of claim 1, further comprising, producing a hydrocarbon from the depth determined using the data set.

12. One or more machine-readable hardware storage devices comprising instructions that are executable by one or more processing devices to perform operations comprising the method of claim 1.

13. A system comprising:

one or more processing devices; and one or more machine-readable hardware storage devices comprising instructions that are executable by the one or more processing devices to perform operations comprising the method of claim 1.

14. The method of claim 1, wherein:

the method further comprises measuring a clastic content of the samples; and the data set further comprises the measured clastic content versus depth of the formation.

15. A method of determining a depth of source rocks within a formation, the method comprising:

measuring a carbon isotope ratio from samples taken at a plurality of depths from a formation;

generating a data set comprising the carbon isotope ratio versus depth; and using the data set to determine a depth of the source rocks within the formation;

wherein using the data set to determine the depth of the source rocks within the formation comprises:

identifying a positive shift in the measured carbon isotope ratio followed by a local maximum value in the measured carbon isotope ratio as the depth decreases, wherein the local maximum value in the measured carbon isotope ratio as the depth decreases corresponds to the depth of the source rocks.

16. The method of claim 15, wherein a negative shift in the measured carbon isotope ratio occurs after the local maximum in the measured carbon isotope ratio as the depth decreases.

17. The method of claim 16, wherein a negative shift in the measured carbon isotope ratio occurs before the positive shift in the measured carbon isotope ratio as the depth decreases.

18. One or more machine-readable hardware storage devices comprising instructions that are executable by one or more processing devices to perform operations comprising the method of claim 15.

19. A system comprising:

one or more processing devices; and one or more machine-readable hardware storage devices comprising instructions that are executable by the one or more processing devices to perform operations comprising the method of claim 15.

20. The method of claim 15, wherein at least one of the following holds:

the method further comprises measuring a strontium isotope ratio of the samples and the data set further comprises the measured strontium isotope ratio versus depth of the formation;

the method further comprises measuring redox sensitive element content of the samples and the data set further comprises the measured redox sensitive element content versus depth of the formation;

the method further comprises measuring a carbonate content of the samples and the data set further comprises the measured carbonate content versus depth of the formation; or the method further comprises measuring a clastic content of the samples and the data set further comprises the measured clastic content versus depth of the formation.

* * * * *